US008038655B2

(12) United States Patent
Burren et al.

(10) Patent No.: US 8,038,655 B2
(45) Date of Patent: Oct. 18, 2011

(54) LATCHING CONTROL DEVICE

(75) Inventors: Stefan Burren, Bremgarten (CH);
Ulrich Moser, Heimiswil (CH);
Christian Schrul, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 1103 days.

(21) Appl. No.: 11/762,521

(22) Filed: Jun. 13, 2007

(65) Prior Publication Data
US 2008/0015514 A1    Jan. 17, 2008

Related U.S. Application Data

(63) Continuation of application No. PCT/CH2005/000546, filed on Sep. 15, 2005.

(30) Foreign Application Priority Data

Dec. 14, 2004   (DE) .......................... 10 2004 060 145

(51) Int. Cl.
*A61M 5/00* (2006.01)
(52) U.S. Cl. ...................................................... 604/209
(58) Field of Classification Search ........... 604/207–211
See application file for complete search history.

(56) References Cited

U.S. PATENT DOCUMENTS

| 4,099,548 | A | * | 7/1978 | Sturm et al. ..................... 141/27 |
| 4,936,833 | A | * | 6/1990 | Sams ............................. 604/232 |
| 5,496,293 | A | * | 3/1996 | Huggenberger .............. 604/208 |
| 5,807,346 | A | | 9/1998 | Frezza et al. |
| 6,007,515 | A | * | 12/1999 | Epstein et al. .................. 604/82 |
| 6,613,023 | B2 | * | 9/2003 | Kirchhofer et al. ........... 604/208 |
| 7,749,201 | B2 | * | 7/2010 | Burren et al. .................. 604/208 |
| 2001/0051792 | A1 | | 12/2001 | Kirchhofer et al. |
| 2003/0187405 | A1 | | 10/2003 | Gatti et al. |

FOREIGN PATENT DOCUMENTS

DE   19948988 A1    4/2000

* cited by examiner

*Primary Examiner* — Theodore Stigell
*Assistant Examiner* — Andrew Gilbert
(74) *Attorney, Agent, or Firm* — Dorsey & Whitney LLP; David E. Bruhn, Esq.

(57) ABSTRACT

A dose metering mechanism for use in administering doses of an injectable product from an injection device, the dose metering mechanism including a rack with teeth, a feed sleeve displaceable relative to the rack, a first catch element associated with the feed sleeve for latching in the teeth of the rack, a guide piece relative to which the rack is movable, a second catch element associated with the guide piece for latching in the teeth of the rack, and a latching control device associated with the toothed rack for controlling the latching of at least one of the first and second catch elements in the teeth of the rack. A method of preparing to administer and administering doses of an injectable product from an injection device including the dose metering mechanism is encompassed.

11 Claims, 3 Drawing Sheets

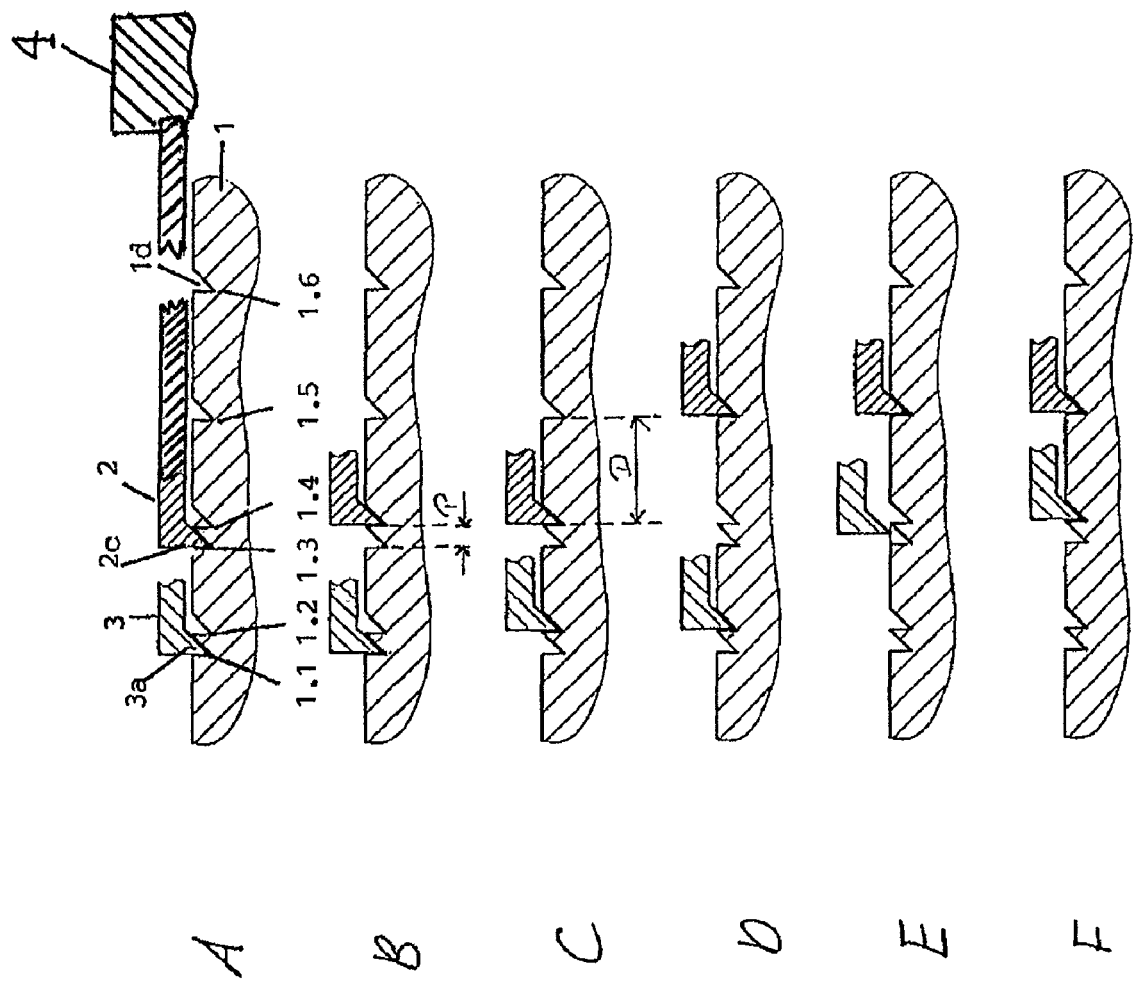

LATCHING CONTROL DEVICE

CROSS-REFERENCE TO RELATED APPLICATIONS

This application is a continuation of International Application No. PCT/CH2005/000546, filed on Sep. 15, 2005, which claims priority to German Application No. DE 10 2004 060 145.3 filed on Dec. 14, 2004, the contents of both of which are incorporated in their entirety herein by reference.

BACKGROUND

The present invention relates to devices for delivering, injecting, dispensing, infusing or administering substances, and to methods of making and using such devices. More particularly, it relates to an injection device comprising a dose metering mechanism for selecting and/or administering doses of an injectable product. More particularly, it relates to a dose metering mechanism comprising a latching control device for controlling the latching action of catch elements of a feed sleeve and a guide piece in the teeth of a toothed rack to enable a priming dose and another dose to be dispensed, wherein the priming and another doses may be different, set or selected easily and in a user-friendly manner, and dispensed from the injection device.

When using injection devices, for example injection pens, with which a substance such as a medicinal substance or a medicament, e.g., insulin, hormones, etc., can be administered in doses, it is customarily first necessary to set what is referred to as a priming quantity or dose which has to be dispensed during priming. Generally, the purpose of priming is to vent an injection cannula associated with the injection device, with a view to freeing the cannula of any residual substances and/or air. Generally, this is done by ejecting a specific small quantity of the product to be injected from the cannula or needle of the injection device without actually administering an injection. The dose or amount of the substance to be injected, which is usually bigger than the priming amount, can then be set and/or injected.

In a known injection device, teeth are provided on a toothed rack at a constant distance apart, in which snappers or engagement structures of a feed sleeve and a guide sleeve can engage. The teeth of the toothed rack can be pushed past the guide sleeve to dispense the substance from the injection device, and the snapper of the guide sleeve latching in the teeth causes an additional clicking sound during the dispensing operation, which can unsettle the user during the injection.

SUMMARY

An object of the present invention is to provide a dose metering mechanism for use in administering doses of an injectable product from an injection device, wherein the dose metering mechanism contributes to and enables simple, user-friendly operation of the injection device.

In one embodiment, the present invention comprises a dose metering mechanism for use in administering doses of an injectable product from an injection device, the dose metering mechanism comprising: a rack with teeth, a feed sleeve displaceable relative to the rack, a first catch element associated with the feed sleeve for latching in the teeth of the rack, a guide piece relative to which the rack is movable, a second catch element associated with the guide piece for latching in the teeth of the rack, and a latching control device associated with the toothed rack for controlling the latching of at least one of the first and second catch elements in the teeth of the rack. A method of preparing to administer and administering doses of an injectable product from an injection device including the dose metering mechanism is encompassed.

In one embodiment, the present invention comprises a method of preparing to administer doses of an injectable product from an injection device comprising a priming system, the method comprising the steps of:

effecting a pulling movement of the injection device by moving a setting element or knob opposite to a dispensing direction of the injectable product, the movement of the setting element or knob causing a feed sleeve to be moved opposite to the dispensing direction of the injectable product relative to a rack which remains stationary due to a catch element associated with a guide piece latching with the rack, and blocking the pulling movement after a predefined distance by stopping the feed sleeve using a stop and a counter-stop and latching a catch element of the feed sleeve with the rack, whereby, due to the movement of the setting element or knob in the dispensing direction of the injectable product, the feed sleeve moves the rack in the dispensing direction relative to the guide piece, and a first dose, which may be thought of as a priming dose, is dispensed due to the movement of the rack and wherein, after the relative movement between the rack and guide piece, the catch element of the guide piece latches with the rack.

In one embodiment, the dose metering mechanism provided by the present invention for administering doses of an injectable product from an injection device has a toothed rack with at least one set of teeth, the teeth extending at least partially across a surface of the toothed rack, and a feed sleeve, on which at least one catch element or latching element such as a snapper, suitably shaped protuberance or engagement structure is disposed. The dose metering mechanism further comprises a guide piece with a catch or latching element, such as a snapper, which also may take the form of, be thought of and/or referred to as a suitably shaped end or tip portion of an arm or a suitably shaped engagement structure, which is able to locate or latch in the teeth of the toothed rack. The feed sleeve may be connected to a setting element or a knob, which can be used to set a priming quantity and/or a dose quantity and for pulling the dose metering mechanism or the injection device so that the feed sleeve can be moved relative to the toothed rack, which is retained by an element of the guide piece, by moving the setting element in the direction opposite that in which the injectable product is dispensed from the injection device. The displaceable feed sleeve can be pushed or moved in the pulling direction of the setting element and in the direction opposite that in which the injectable product is dispensed by moving the setting element or knob. When the feed sleeve is moved relative to the toothed rack in the direction opposite the dispensing direction, the catch element or latching element of the feed sleeve located or latched in the teeth of the toothed rack is released from the teeth of the toothed rack and effects a relative movement with respect to the toothed rack together with the feed sleeve.

In some embodiments, the guide piece or guide sleeve may be connected to the injection device in such a way that when the setting element or knob is moved or pressed in the dispensing direction of the injectable product, the feed sleeve, in particular the catch element of the feed sleeve latching in the teeth of the toothed rack, transmits or exerts a force or a pressure via the teeth to or on the toothed rack and the toothed rack moves in the dispensing direction, as a result of which the toothed rack is moved relative to the guide piece. Due to the relative movement of the rack with respect to the guide piece, the catch element or latching element of the guide piece engaging or latching in the teeth of the rack moves radially outwardly and is released from the recess of the teeth and effects a movement relative to the toothed rack in the direction opposite the dispensing direction of the injectable product and in the pushing direction of the setting element.

In some embodiments, the dose metering mechanism further comprises a tooth latching control device, which is provided along or on the toothed rack to control or permit control of the catch element of the feed sleeve and/or the catch element of the guide piece latching in the teeth of the toothed rack, e.g., to prevent this or permit it. In some preferred embodiments, the tooth latching control device is provided in the form of at least one rail next to or on the teeth of the rack and may extend at least partially along the longitudinal axis of the rack or injection device. The latching control device may extend along the longitudinal axis of the rack in the form or one or two or more rails, in which case the rail or rails or the curve or curves may extend next to or on the teeth of the rack, thereby enabling the latching action of the catch element of the feed sleeve and/or the guide piece in the teeth or in the recesses or grooves provided in the rack to be permitted, prevented and/or controlled. In some preferred embodiments, the latching control device prevents the catch element or latching element of the feed sleeve and/or the guide piece or guide sleeve in the teeth of the rack from engaging or latching on the teeth or at positions of the teeth at which the latching control device is provided or where the latching control device is disposed along or on the rack.

In some preferred embodiments, the teeth of the toothed rack, in conjunction with the latching control device provided along, adjacent to or on the rack, forms a dispensing profile on the rack, by which a priming quantity and/or a predefined dose quantity of the injectable product can be set and/or dispensed, such as a dose quantity set using the setting element or setting knob. This being the case, the dispensing profile is defined by the length, the position and/or the shape of the latching control device, e.g., a rail or curve associated with the rack, and the latching control device and/or the shape or the position of the latching control device determines at which teeth or at which points of the teeth the catch element of the feed sleeve and/or the catch element of the guide piece can latch, engage or locate in the teeth or recesses between the teeth of the rack.

In preferred embodiments, the catch element of the guide piece and the catch element of the feed sleeve are of an identical width so that in the absence of the tooth latching control device, both catch elements can reliably engage in the same or all of the teeth of the toothed rack. The latching control device may be shaped or positioned in such a way that the catch element of the feed sleeve is able to locate in different teeth or at different points of the teeth of the rack than the catch element of the guide piece, or the catch element of the guide piece and/or the latching control device are able to prevent or permit latching of the catch element of the feed sleeve in the teeth of the rack, e.g., due to the shape and/or the position of the latching control device. For example, the tooth latching control device may be provided in the form of a rail or curve next to the teeth of the rack in the longitudinal direction of the rack, in which case the catch element of the guide piece and the catch element of the feed sleeve may be disposed offset from one another in the transverse direction relative to the rack by a predefined value or distance. Thus, when there is a relative movement of the feed sleeve with respect to the rack in the longitudinal direction of the rack and/or opposite the dispensing direction, the catch element of the feed sleeve is not guided by the rail serving as a latching control device, but is able to locate or engage in each of the teeth or in each of the recesses between the teeth during the movement. When the guide piece moves relative to the rack, on the other hand, the catch element of the guide piece is guided or pushed at least partially across or on the rail or curve structure so that the rail or curve prevents the catch element or latching element of the guide piece from latching or connecting with the teeth or at the positions of the teeth next to which the rail is disposed.

In some preferred embodiments, the catch element of the guide piece may be wider than the catch element of the feed sleeve so that the latching control device is able to prevent the catch element of the guide piece from latching or locating in the teeth or at the positions of teeth next to, where or in which the latching control device is provided, e.g., due to the shape or position of the latching control device. For example, the latching control device may be provided in the form of a rail or as two or more rails adjacent to, along or on the rack, in some embodiments, next to the teeth of the rack.

If, as is the case in some embodiments, the catch element of the guide piece is wider than the catch element of the feed sleeve, for example, and if the latching control device is provided in the form of one or two or more rails or curves extending next to the teeth and the width of the catch element of the feed sleeve corresponds at most to approximately the width of the teeth and the width of the catch element of the guide piece corresponds at least approximately to the width of the teeth, in some preferred embodiments approximately the width of the teeth and the rails or curves, when the feed sleeve effects a relative movement with respect to the rack, the catch element of the feed sleeve is not guided, pushed or moved via the rails and is able to engage in every tooth or at every point of the teeth of the rack. When the catch element of the guide piece effects a relative movement with respect to the rack, on the other hand, the catch element of the guide piece is guided, pushed or moved on the teeth or at positions of the teeth across or on the rail where the rail or rails are provided or disposed, so that the catch element of the guide piece is prevented from latching or locating in these teeth or at the selected positions.

In some preferred embodiments, the toothed rack may have a rectangular cross-section and teeth may be provided on one, two, three or four sides of the rack. This being the case, all the sides of the toothed rack may have the same or a different dispensing profile, which may be determined by the shape and/or the position of the teeth and/or the latching control device, or it may be that two respective sides of the toothed rack match one another in terms of the dispensing profile, in which case oppositely lying sides may specifically have the same dispensing profile. In some preferred embodiments, the rack may be mounted so that it can be removed or rotated, for example by rotating the setting element or knob or by re-fitting or re-inserting the rack after rotating it, so that a different dispensing profile can be aligned with or point in the direction of the catch elements of the guide piece and/or feed sleeve, thereby enabling different dispensing quantities of the injectable product to be set and/or dispensed depending on the different dispensing profiles of the rack.

In some embodiments, the present invention comprises an injection device with a dose metering mechanism of the type described above.

In some embodiments, the toothed rack of the injection device is designed so that a priming quantity of the injectable product can be dispensed from the injection device when, having pulled on the injection device by the setting element or the knob, the feed sleeve or catch element of the feed sleeve is pushed or moved by a priming distance corresponding to the distance between two adjacent teeth of the toothed rack in the pulling direction or opposite the dispensing direction relative to the toothed rack so that the catch element of the feed sleeve is able to latch in the adjacent tooth.

In some preferred embodiments, the toothed rack of the injection device may also be designed so that once the feed sleeve or catch element of the feed sleeve has been moved by a dose setting distance relative to the rack in the pulling direction or opposite the dispensing direction, a dose quantity of the injectable product can be dispensed, and the dose setting distance may correspond to the distance between two teeth in the longitudinal direction which are separated from one another by the tooth latching control device, such as a rail or curve next to or on the teeth.

The present invention further encompasses a method of priming or preparing for administering doses of an injectable product from an injection device of the type set forth above, whereby a first pulling movement of or on the injection device is effected by moving a setting element or knob in the direction opposite that in which the injectable product is dispensed. Due to the movement of the setting element or knob, a feed sleeve is moved opposite the direction in which the injectable product is dispensed relative to a toothed rack, which remains stationery because a catch element of a guide piece latches with the teeth of the toothed rack. The pulling movement is blocked or stopped after a predefined distance by a stop of the feed sleeve which abuts with a counter-stop, and a catch element of the feed sleeve latches with the teeth of the toothed rack so that when the setting element or knob is moved in the dispensing direction of the injectable product, the feed sleeve moves the toothed rack in the dispensing direction relative to the guide piece. As a result, a first dose, for example a priming dose, is dispensed due to the sliding action or movement of the toothed rack for priming purposes and, after the relative movement between the rack and guide piece, the catch element of the guide piece latches in the teeth of the rack.

BRIEF DESCRIPTION OF THE DRAWINGS

FIG. 4 is a schematic longitudinal section showing the device of FIGS. 1-3 in different operating modes or functional states.

DETAILED DESCRIPTION

Figure 1:
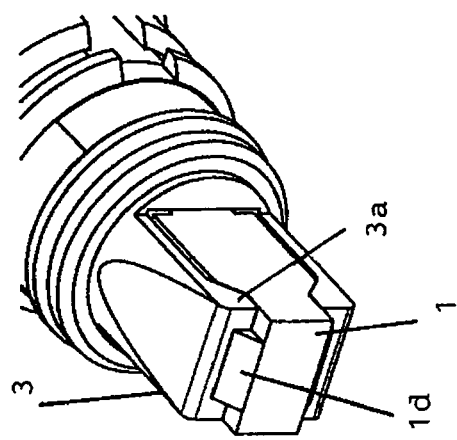
FIGS. 1-3 illustrate an exemplary embodiment of a dose metering mechanism in accordance with the present invention in different operating modes or functional states.
Figure 2:
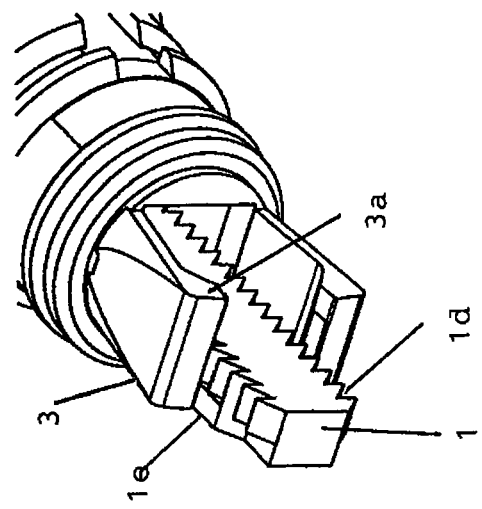
Figure 3:
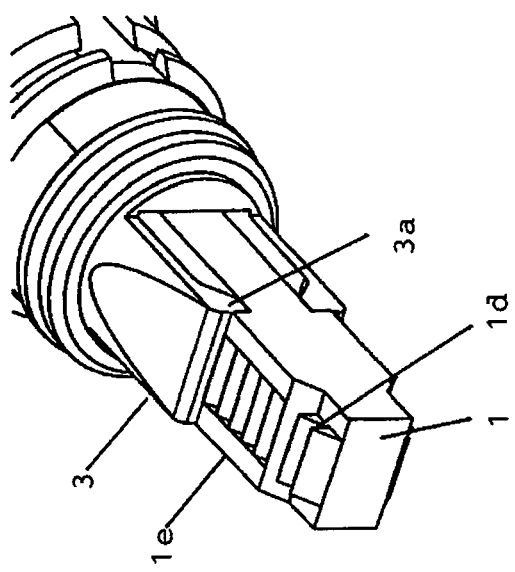

FIGS. 1-3 illustrate a first exemplary embodiment of a dose metering mechanism in accordance with the present invention in different operating modes or functional positions. The dose metering mechanism may be located at or form the rear end of an injection device. Referring to FIG. 1, the dose metering mechanism comprises a toothed rack 1 comprising a set of teeth 1d comprising a row of consecutive teeth lying between a guide piece 3. The toothed rack can be pushed onto or against a stopper of an ampoule (not illustrated) at the front end of the toothed rack illustrated at the front in FIG. 1, to effect a dispensing procedure from an injection device by a movement of the toothed rack 1 forward, i.e., at an angle in FIG. 1. The teeth of the toothed rack 1 are of a sawtooth design, and the respective sides or faces of the sawtooth teeth which do not stand vertically with respect to the toothed rack 1 point in the dispensing direction of the injectable product and the sides of the sawtooth teeth which stand vertically with respect to the toothed rack 1 point in a pulling direction of the injection device or, in other words, opposite to the dispensing direction. The recesses formed by the teeth of the toothed rack 1 or grooves of the teeth each have a side or face standing vertically relative to the rack and facing in the dispensing direction of the injectable product and a non-vertical side which faces in the direction opposite the dispensing direction or in the pulling direction of the injection device. Disposed around the toothed rack 1 is a feed sleeve (not illustrated) and a guide piece 3, both of which have a flexible arm, snapper or a catch element 3a in accordance with the present invention, which can be moved radially inwardly and outwardly and which locate or lodge in a first recess of the teeth 1d of the toothed rack 1 or behind a first tooth of the teeth 1d in the position illustrated in FIG. 1. Although not visible in FIG. 1, the catch element or snapper of the feed sleeve also engages the catch element 3a of the guide piece 3 in a recess of the toothed rack 1 or between two teeth of the teeth 1d.

When a dispensing quantity of the injectable product is set on a setting element or knob of the dose metering mechanism, a pulling action on the setting element used to effect a pulling movement opposite the dispensing direction of the injectable product (toward the rear in FIG. 1) causes the feed sleeve connected to the setting element to move opposite the dispensing direction so that the catch element of the feed sleeve can latch in a recess in the teeth 1d of the toothed rack 1 after a path or distance which enables the injectable product to be dispensed in the set quantity or corresponding to the dispensing quantity. When the setting element or the knob is pushed in the dispensing direction, the feed sleeve, in particular the catch element, snapper or flexible arm of the feed sleeve, exerts a force in the dispensing direction on the teeth 1d of the toothed rack or on the toothed rack 1, or transmits a forward pushing force via the teeth 1d to the toothed rack 1, as a result of which the toothed rack 1 is moved in the dispensing direction relative to the guide piece 3 and the flexible arm or the catch element 3a of the guide piece 3 is forced radially outwardly, as illustrated in FIG. 2.

FIG. 2 illustrates a transition position of the dose metering mechanism during a dispensing operation, in which the toothed rack 1 is moved relative to the guide piece 3, the catch element 3a of the guide piece 3 lies on the tooth latching control device 1e, that is, on at least one or two rails next to the teeth 1d of the toothed rack 1 and therefore does not latch in the teeth next to which the at least one tooth latching control device is disposed or provided. When the set dose of the injectable product has been dispensed on completion of the dispensing operation, the tooth latching control device 1e in the form of a rail terminates so that the catch element 3a or snapper of the guide piece 3 is able to latch or locate in the following tooth on the rail, which is perceptible to the user of the dose dispensing or injection device due to a clicking noise.

FIG. 4 illustrates the sequence of the dispensing operation in schematic longitudinal sections A-F of the dose metering mechanism in different positions or steps of the dispensing operation. In position A, the catch element 3a or protruding snapper or tip portion of the guide piece 3 is disposed in a recess 1.1 of the teeth 1d of the toothed rack 1 and the catch element 2c or latching snapper of the feed sleeve 2 is disposed in a recess 1.3 of the toothed rack 1. By pulling a setting element 4 or knob connected to the feed sleeve, the catch element 2c of the feed sleeve 2 is moved radially outwards and is moved out of or pulled out of the recess 1.3 and, after being moved or pushed by a priming distance P, latches in the subsequent recess 1.4 of the teeth 1d.

When the setting element 4 is pushed in the dispensing direction, toward the left in FIG. 4, the catch element 2c exerts a force or pressure on the teeth 1d of the rack 1 or on the rack 1 in the dispensing direction due to the shape of the teeth 1d and/or the shape of the catch element 2c of the feed sleeve 2. Thus, the toothed rack 1 is moved or pushed in the dispensing direction by the priming distance P. As a result, the catch element 3a of the guide piece 3 is forced outward due to the shape of the recesses of the teeth 1d and/or the relative movement of the toothed rack 1 or of the guide piece 3, the toothed rack 1 effects a relative movement by the priming distance P with respect to the catch element 3a of the guide piece 3, and the catch element 3a of the guide piece 3 is pushed out of the recess 1.1 and latches or locates in the subsequent recess 1.2 of the teeth 1d of the toothed rack 1, as illustrated in step C. Due to the forward movement by the priming distance P in the dispensing direction, the front end of the toothed rack 1, which lies at the left-hand side of the toothed rack 1 in FIG. 4, pushes against a stopper of an ampoule (not illustrated), thereby causing a dispensing operation of a priming quantity of the injection device.

When a dose quantity is set at the setting element 4, e.g., a knob for example, the setting element 4 and, thus, the feed sleeve connected thereto can be pulled by a dose setting distance D opposite the dispensing direction so that the catch element 2c of the feed sleeve 2 can be moved or pushed by the dose setting distance D opposite the dispensing direction and in the pulling direction out of the recess 1.4 into a recess 1.5 of the toothed rack 1 and can latch in the recess 1.5 which is disposed at a distance from the recess 1.4 corresponding to the dose setting distance D. When the setting element 4 is pushed in the dispensing direction, the catch element 2c of the feed sleeve 2 transmits a force in the dispensing direction via the teeth 1d to the toothed rack 1, as a result of which the toothed rack 1 is pushed or moved by the dose setting distance D relative to the guide piece 3. The catch element 3a of the guide piece 3 is pushed or forced radially outwards out of the recess 1.2 and runs along the tooth latching control device 1e provided in the form of a rail extending next to the teeth 1d, as illustrated in step E, so that the catch element 3a of the guide piece 3 does not latch in the recess 1.3 of the teeth 1d next to which the rail or tooth latching control device 1e is disposed and does not latch until reaching the recess 1.4 next to which no rail or tooth latching control device 1e is provided.

After the dispensing operation, the dose metering mechanism is in position F and, due to the presence of the tooth latching control device 1e, makes only one clicking noise due to the catch element 3a of the guide piece 3 latching in the recess 1.4, next to which no tooth latching control device is provided. However, no additional clicking noise is caused by the catch element 3a of the guide piece 3 latching in the recess 1.3 because this is where the rail serving as a latching control device runs or extends and the catch element 3a of the guide piece 3 is prevented from latching in the recess 1.3 of the teeth 1d by the rail serving as a tooth latching control device.

Figure 5A:
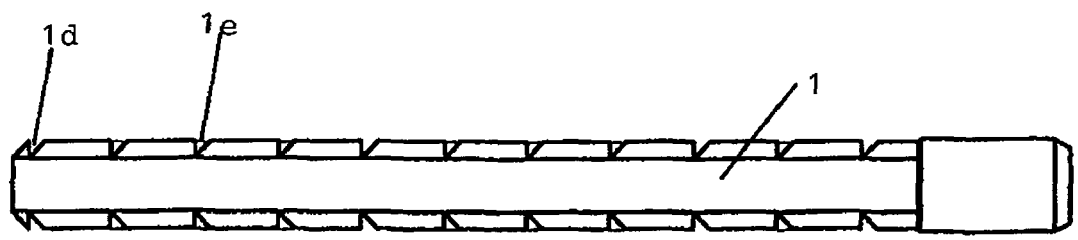
FIG. 5 illustrates a toothed rack of another embodiment of the dose metering mechanism in accordance with the present invention.
Figure 5B:
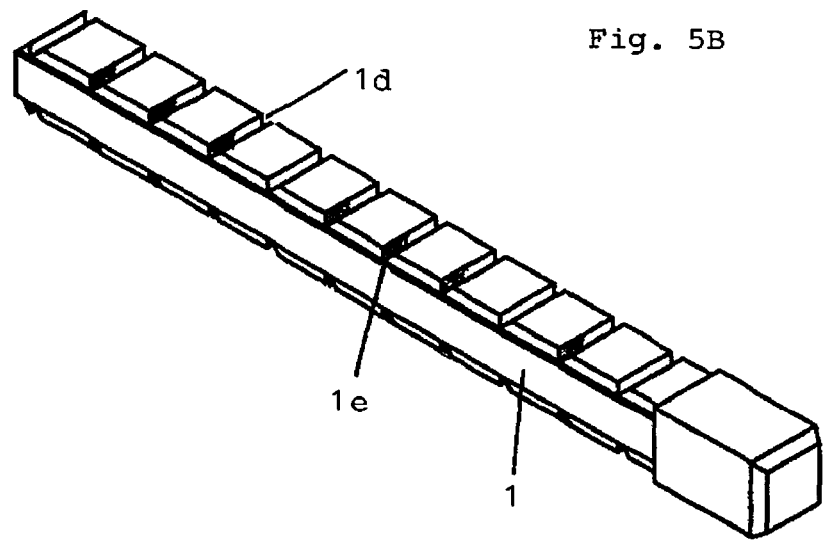

FIGS. 5a and 5b illustrate an embodiment of a toothed rack 1 of the dose metering mechanism and/or injection device in accordance with the present invention, in which grooves or recesses are provided as teeth 1d in the toothed rack 1, in which the catch elements of the feed sleeve and/or the guide piece can latch or locate. In this instance, some of the grooves or recesses are provided with a tooth latching control device 1e or are at least partially filled by the tooth latching control device 1e so that, for example, the catch element of the feed sleeve is able to latch in all the recesses or teeth but the catch element of the guide piece, which is wider, is only able to latch in recesses in which no tooth latching control device 1e is provided and can not latch in recesses or teeth or grooves which are at least partially filled with a tooth latching control device 1e or at least partially contain a tooth latching control device 1e. The feed sleeve and the guide piece of this arrangement may be offset from one another in the transverse direction, in which case the tooth latching control device 1e does not have to be provided at the edge of the toothed rack or recesses as illustrated in FIGS. 5a and 5b, but may be disposed at any point of the recesses or toothed rack, and the catch element of the guide piece may be designed or shaped so that it can not latch in the recesses of the teeth 1d in which the tooth latching control device 1e is provided or contained, and the catch element of the feed sleeve is respectively shaped or designed so that it can locate in all the recesses, irrespective of whether the tooth latching control device 1e is disposed in the recess or provided on the recess.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a dose metering mechanism comprising:
    a rack with teeth;
    a feed sleeve displaceable relative to the rack, with a catch element for latching in the teeth of the rack;
    a guide piece with a catch element for latching in the teeth of the rack, the rack being movable relative to the guide piece; and
    a tooth latching control device associated with the rack and able to control the latching action of at least one of the catch element of the feed sleeve and the catch element of the guide piece in the teeth of the rack; wherein
    the tooth latching control device comprises at least one rail which prevents the catch element from engaging or latching in the teeth of the rack in positions in which the tooth latching control device is on the rack or on the rack and extending along and next to the teeth.

2. A dose metering mechanism for administering doses of an injectable product from an injection device comprising:
    a rack with teeth;
    a feed sleeve displaceable relative to the rack, with a catch element for latching in the teeth of the rack;
    a guide piece with a catch element for latching in the teeth of the rack, the rack being moveable relative to the guide piece;
    a tooth latching control device associated with the rack and able to control the latching action of at least one of the catch element of the feed sleeve and the catch element of the guide piece in the teeth of the rack; wherein
    the tooth latching control device comprises at least one rail which prevents the catch element from engaging or latching in the teeth of the rack in positions in which the tooth latching control device is on the rack or on the rack and extending along and next to the teeth.

3. The dose metering mechanism as claimed in claim 2, further comprising a setting element for setting at least one of a priming quantity and a dose quantity.

4. The dose metering mechanism as claimed in claim 2, wherein the teeth of the rack create a dispensing profile on the rack by which at least one of a priming quantity and predefined dose quantities of the injectable product can be set.

5. The dose metering mechanism as claimed in claim 2, wherein the catch element of the guide piece and the catch element of the feed sleeve have substantially identically widths.

6. The dose metering mechanism as claimed in claim 2, wherein the catch element of the guide piece is wider than the catch element of the feed sleeve, whereby the catch element of the guide piece is prevented from latching in the teeth with which the tooth latching control device is associated, and the catch element of the feed sleeve can latch in the teeth.

7. The dose metering mechanism as claimed in claim 4, wherein the rack has a rectangular cross-section.

8. The dose metering mechanism as claimed in claim 4, wherein the rack has two generally opposite sides, each of said sides having the same dispensing profile.

9. The dose metering mechanism as claimed in claim 7, in which each side of the rack has a different dispensing profile.

10. The injection device according to claim 1, wherein the distance between two adjacent teeth corresponds to a priming distance and, after moving the feed sleeve the priming distance relative to the rack, a priming quantity of the injectable product can be dispensed from the injection device.

11. The injection device according to claim 10, wherein the distance between two teeth which are separated from one another by the latching control device creates a dose setting distance and, after moving the feed sleeve by the dose setting distance relative to the rack, a dose quantity of the injectable product can be dispensed.

* * * * *

UNITED STATES PATENT AND TRADEMARK OFFICE
CERTIFICATE OF CORRECTION

Page 1 of 1

PATENT NO. : 8,038,655 B2
APPLICATION NO. : 11/762521
DATED : October 18, 2011
INVENTOR(S) : Stefan Burren et al.

It is certified that error appears in the above-identified patent and that said Letters Patent is hereby corrected as shown below:

SPECIFICATION

| Column | Line | PTO | Should Read |
|---|---|---|---|
| 5 | 58 | "a set of teeth id" | -- a set of teeth 1d -- |

Signed and Sealed this
Twentieth Day of December, 2011

David J. Kappos
*Director of the United States Patent and Trademark Office*